United States Patent
Eek

(10) Patent No.: US 8,048,865 B2
(45) Date of Patent: Nov. 1, 2011

(54) METHOD AND PHARMACEUTICAL TO TREAT SPINAL DISCS

(76) Inventor: Bjorn C. J. Eek, Long Beach, CA (US)

(*) Notice: Subject to any disclaimer, the term of this patent is extended or adjusted under 35 U.S.C. 154(b) by 0 days.

(21) Appl. No.: 12/643,807

(22) Filed: Dec. 21, 2009

(65) Prior Publication Data

US 2011/0003770 A1    Jan. 6, 2011

Related U.S. Application Data

(63) Continuation of application No. 11/210,307, filed on Aug. 24, 2005, now abandoned, which is a continuation-in-part of application No. 10/441,130, filed on Oct. 4, 2002, now abandoned, which is a continuation-in-part of application No. 09/704,267, filed on Oct. 31, 2000, now abandoned.

(51) Int. Cl.
  *A01N 43/04*   (2006.01)
  *A61K 31/715*  (2006.01)
  *A61K 31/60*   (2006.01)

(52) U.S. Cl. ............................................. 514/45; 514/62

(58) Field of Classification Search ........................ None
  See application file for complete search history.

(56) References Cited

U.S. PATENT DOCUMENTS

| | | | |
|---|---|---|---|
| 5,470,842 | A  | 11/1995 | Brandley et al. |
| 6,046,187 | A  | 4/2000  | Berde et al. |
| 6,255,295 | B1 | 7/2001  | Henderson et al. |
| 6,335,035 | B1 | 1/2002  | Drizen et al. |
| 6,476,005 | B1 | 11/2002 | Petito et al. |
| 6,562,873 | B2 | 5/2003  | Olejnik et al. |

OTHER PUBLICATIONS

Klein et al., "Biochemical injection treatment for discogenic low back pain: a pilot study," *The Spine Journal*, 3:220-226(2003).
Simon, "Osteoarthritis: A Review," *Clinical Cornerstone*, 2(2):26-37 (1999).

*Primary Examiner* — Layla Bland
(74) *Attorney, Agent, or Firm* — O'Melveny & Myers LLP

(57) ABSTRACT

Methods for reducing chronic pain caused by a disrupted spinal disc are described. In one method, a physiologically acceptable amount of an injectable is injected into the disc. The injectable is obtained from a stock solution comprising chondroitin sulphate, glucosamine HCl, aqueous solution of dextrose; sodium carboxymethylcellulose, and a buffer substance in quantity to bring the pH of the stock solution to a value above about 6.0. Water is also added to dilute the stock solution. The stock solution may further comprise an anesthetic such as bupivicaine.

8 Claims, No Drawings

METHOD AND PHARMACEUTICAL TO TREAT SPINAL DISCS

CROSS-REFERENCE TO PRIOR APPLICATION

This application is a continuation of U.S. application Ser. No. 11/210,307, filed Aug. 24, 2005 now abandoned, which is a continuation-in-part of U.S. application Ser. No. 10/441,130, filed Oct. 4, 2002, now abandoned, which is a continuation-in-part of U.S. application Ser. No. 09/704,267, filed Oct. 31, 2000, now abandoned, all of which are expressly incorporated herein by reference in their entirety.

FIELD OF THE INVENTION

An injectable for and a method of use to treat spinal discs.

BACKGROUND OF THE INVENTION

The human skeleton has evolved to allow for upright posture and bipedal motion. The human spine in its development to support the upright body has developed areas of stress particularly at the base of the neck, the apex of the mid back (thoracic spine) and in the lower back (lower lumbar spine). The spine is formed by bony elements, the vertebrae, and cushions between vertebrae, the intervertebral discs. The spine is then supported by ligaments, fibrous bands of tissue that join bones together, and muscles and fascia, which provide dynamic support and zygapophyseal joints, two at each level posteriorly which join the vertebrae together. Anteriorly the intervertebral disc serves as a cushion between the vertebrae but also helps join the vertebrae together and provides stability.

When neck or back pain becomes chronic, usually due to injury or repetitive stress, and the pain becomes severe and limiting or disabling the intervertebral disc(s) is/are the source of pain.

The most common cause of disability below the age of forty-five is chronic low back pain. Chronic low back pain is due to intervertebral disc disease in forty percent of patients, zygapophyseal joint dysfunction is fifteen to thirty percent of patients, sacra-iliac joint complex dysfunction in fifteen percent of patients, and in the remaining fifteen percent, multiple causes.

When an intervertebral disc becomes injured, the natural reparative process is often hindered due to limited blood supply to the inner portion of the intervertebral disc. Normally blood vessels are found only in the outer third of the peripheral portion of the disc, the annulus. However nutrition to the central portion of the disc depends upon perfusion of nutrients through the vertebral end-plate which separates the disc from the body of the vertebra above and below.

When nutrition becomes impaired the disc tissue becomes acidic and a degenerative process usually ensues. If the normal reparative process is inadequate, the disc can continue to degenerate and be the source of pain. The degenerative process varies in extent in every intervertebral disc that is chronically painful. A chemical reaction occurs within the disc usually at the site of injury. The chemicals cause further breakdown of the disc and when the chemicals escape into the spinal canal inflammation occurs and affects the spinal nerves causing further pain. In older patients (35 years plus) where degeneration is present the pain is not only due to a chemical reaction within the disc but instability of the disc secondary to previous degeneration.

Low back pain is reaching epidemic proportions in the Western world. Traditionally the treatment for severe discogenic pain has been surgical removal of the injured intervertebral disc and fusion of the spine surgically by replacing the disc with bone graft or various metal implants containing bone graft. This procedure is very expensive. Costs can range up to one hundred thousand dollars. It requires from six months to one year to recover. Up to eighty percent of the fusions become solid. However pain improvement is problematical. At best fifty to sixty percent of patients experience pain reduction, not always completely. Up to fifty percent remain with the same degree of pain or worse. The latter group often becomes permanently disabled and dependent upon opioid medications.

Upon evaluation of back pain many factors must be considered: age, severity of pain, radiation of pain into buttock or legs, and the presence of leg numbness or weakness. Commonly most patients who suffer an initial injury can recover fully if they rest appropriately, and inflammation within or about the disc is addressed. Thereafter a conditioning program becomes important in order to strengthen the muscles for supporting the trunk and providing controlled movement. When there is recurrence of low back pain after injury or stress the condition usually becomes more serious.

When an intervertebral disc can be identified as a source of pain usually by combination of a MRI scan of the lumbar spine as well as lumbar discography, the latter is a provocative test for discogenic pain by placing a needle into the center of the disc and injection of radiographic contrast under pressure. In a normal disc there is no pain provoked. In an abnormal disc pain is provoked, and if it causes the pain that is experienced by the patient, then the disc is concordantly painful.

At the same time fissures to the outer portion of the disc, the annulus, or multiple tears radiating from the center of the disc, the nucleus, to the periphery of the disc through the annulus are visualized. If the intervertebral disc has normal height, and there is a single fissure, and there is severe pain on low pressure by discogram, then a highly chemically sensitive disc is present. This condition is called an internal disc disruption. If multiple tears are identified, the disc has become narrowed by degeneration, and the pain is less severe but still significant, the condition is often called symptomatic degenerative disc disease.

The traditional treatment to the present time for severe painful discogenic disease has been spinal fusion. Successful results are modest. Therefore it is essential to find simpler and better ways to treat painful intervertebral discs. Several devices have been developed in recent years. At present there are two devices that are used relatively commonly, the first is the IDET (intra-discal electrothermal therapy) and the other is the nucleoplasty.

These two devices have limited use. They can only be used on intervertebral discs that have nearly normal height, have a single fissure and are chemically sensitive. The nucleoplasty is also used when there is posterior bulging of the disc for it will remove or ease the central pressures within the disc and therefore the pressure upon the periphery of the disc is reduced. Their success is partial. No alternative treatment for internal disc disruption or symptomatic degenerative disc disease has been developed until the chemical disc injection treatment (disc restorative solution) of this invention.

DETAILED DESCRIPTION OF THE INVENTION

Observation based upon injection treatment of soft tissue injuries, namely ligaments, tendons and fascia, wherein the injected solution causes a mild inflammatory reaction followed by a reparative response within the tissues, led to the concept that painful and damaged intervertebral discs could be treated similarly. The solution selected to test this hypothesis was the combination of chondroitin sulfate, glucosamine HCl, hypertonic dextrose, bupivacaine and DMSO (dimethyl sulfoxide) when indicated. Because the solution becomes acidic with a pH of 4.3, a buffer solution has also been added to the solution, namely a combination of mono and diphosphates which increases the pH level to above about 6.0, and preferably between about 6.3 to about 6.8 which is slightly acidic but within physiologic range. In some conditions where the annular portion of the intervertebral disc has degenerated significantly and there appears to be inflamed areas within parts of the annulus, then DMSO can be added to facilitate dispersion of the solution. DMSO serves essentially as a solvent.

Chondroitin sulfate and glucosamine hydrochloride are substrates of collagen. Collagen is the basic building block of fibrous tissue, which the annular portion of the disc is comprised.

The hypertonic dextrose stimulates growth factor as well as, it is believed, nourishes the chondrocytes and fibrocytes present within the intervertebral disc, and to some degree serves as a neurolytic agent for unmyelinated sensory nerve fibers that can penetrate the intervertebral disc.

In a recent study done by Klein, Eek et al (manuscript submitted for publication) presented a potential new alternative treatment for chronic disogenic back pain. Thirty patients were included in the study. All of the patients treated had positive discography at one or more levels as evidenced by concordant pain and morphologic disc disruption. The discs were injected with the disc solution as described. Three to four treatments were done at two to three month intervals. The patients were followed for approximately twelve months after completion of treatment. Seventeen patients improved on average seventy-four percent using the Roland-Morris functional questionnaire and the VAS pain scale. Thirteen patients did not improve significantly. These patients fell into varying groups, namely, failed posterior spinal fusion, spinal stenosis, generalized fibromyalgia syndrome, failed IDET procedure etc. Since that time over one hundred patients have been treated. Now the majority of patients are gradually improving. It requires up to a year to gain maximum improvement.

It is believed that the disc restorative solution will mitigate the chemical-inflammatory condition within the disc and will stimulate gradually a reparative response, which will reduce pain and stabilize degenerative discs.

The ingredients are formulated into pharmaceutically acceptable and tolerable carrier such as sterile water or normal saline in accordance with standard pharmaceutical practice. These ingredients are provided in a stock solution, which is then diluted or augmented to the desired concentrations and composition. The formulation is passed through a 2 micron filter.

Common to all formulations according to this invention is the inclusion, in an injectable tolerated by the spinal disc, of both glucosamine and chondroitin sulfate (in a buffered injectable solution). Injections with only one of these constituents have proved to be without value, but their combination in a properly buffered solution has proved to be otherwise.

The dispersion of this solution in the disc appears to be markedly improved by the optional inclusion of dimethyl sulfoxide (DMSO), which is an optional ingredient, but one which appears to provide for greater acceptance in the disc.

Improved stability of the disc and reduction of pain appears to be provided by the incorporation of low viscosity sodium-carboxymethylcellulose, which is also believed to coat sensory unmyelinated nerves in the discs.

Important improvements to the comfort of the patient can be attained in all situations by the further inclusion of a local temporary-acting anaesthetic such as Marcaine (bupivicaine). Any lessening of pain, even during the brief period during and following the injection, can provide important benefits to an apprehensive patient, and reduce the inflammation caused by the insult of the needle and the event of the injection.

The ingredients are formulated into a pharmaceutically-acceptable and tolerable carrier such as sterile water in accordance with good pharmaceutical practice. These ingredients are provided in a stock solution, which is then diluted or augmented to the desired concentrations and composition.

For example, if only the ingredients in this stock solution are desired, an equal volume of water will be added to it, to reduce the concentration by half, thereby providing the injectable. The ratios between the ingredients will not be changed, but their concentration in the injectable will be reduced from what they were in the stock solution.

Improved injectables can be provided by the addition of other substances.

For example, either sodiumcarboxymethylcellulose or a temporary anaesthetic such as Bupivicane can optionally be added to the stock solution in a respective amount of one percent each. This provides a modified stock solution, subject to the same later dilution.

The stock solution (basic or modified) is conveniently made in 2 cc increments subject to later dilution. The sodium carboxymethylcellulose and anaesthetic when used are added to the basic stock solution, to form the 2 cc increment. In both events, 2 cc of water will be added to make the injectable.

Two other optional ingredients can provide additional benefits. They are used as, or part of the diluent, each as 1 cc in place of 1 cc of dilution water.

One such ingredient is dextrose, 50% solution. When added alone, it will be accompanied by 1 cc of dilution water. Then, when combined with the stock solution, it will be about 12.5% of the injectable.

Similarly, a contrast medium with or without an antibiotic of 2 cc can be provided. If only this ingredient is added, it will be accompanied by 1 cc of dilution water. These are provided in suitable physiological amounts.

When both are used, they will replace the dilution water entirely.

The presently preferred injectable is formulated as follows:

| | |
|---|---|
| Glucosamine | 4% |
| Chondroitin | 0.75% |
| Bupivicaine | 0.5% |

Phosphate buffers to about 6.0, preferably about 6.7

The above to make 50% by volume of this injectable, plus 12.5% by volume dextrose, plus 12.5% by volume of a solution of an aqueous solution and or antibiotic.

In suitable injectables, the ratio or glucosamine to chondroitin can vary from about 3:1 to about 10:1. The presently preferred ratio is about 5⅓:1.

A stock solution can be prepared as follows, the components being given by weight percentages:

| | |
|---|---|
| Chondroitin Sulfate | about 0.5% to about 2% |
| Glucosamine HCl | about 5.0% to about 20% |
| Bupivicaine (optional) | about 2.0% to about 4% |

Buffer substances in quantity sufficient to bring the pH above about 6.0.

Sodium mono and di-phosphate are useful.

| | |
|---|---|
| Sterile Water | to make 100% |

The preferred stock solution is as follows:

| | |
|---|---|
| Chondroitin Sulfate | about 1.5% |
| Glucosamine HCl | about 8.0% |

Buffer substances in quantity sufficient to bring the pH above about 6.0.

Sodium mono and di-phosphate are useful

Sterile water to make 100%.

This stock solution will provide a useful injectable when suitable diluted with sterile water.

Chondroitin sulfate is an acidic irritant. Control over the pH of the injectable appears to alleviate some of its irritating effects. Accordingly it has been found that a pH close to neutral, but a bit on the acid side is better tolerated. Experiment has shown that a pH above about 6.0, is useful, preferably about 6.5 to 7.4. A buffer of monobasic sodium phosphate and dibasic phosphate in sterile water functions well for this purpose and is agreeable to the tissues. The actual amount will be determined by observing the pH value of the injectable when the solution is being prepared.

The amount to be injected is for the discretion and judgement of the surgeon. His experience and the "feel" of the syringe will be the best guidance. Several ccs of the injectable will be the usual dosage per disc.

This invention is not to be limited by the embodiments described in the description, which are given by way of example and not of limitation, but only in accordance with the scope of the appended claims.

What is claimed is:

1. A method of reducing chronic pain caused by a disrupted spinal disc comprising injecting a physiologically acceptable amount of an injectable into said disc, the injectable comprising:
    a stock solution comprising:
        chondroitin sulphate, between about 0.5% to about 2.0%;
        glucosamine HCl, between about 5.0% to about 20.0%; and
        aqueous solution of dextrose;
    and water to dilute the stock solution.

2. The method of claim 1, further comprising a buffer in a quantity to bring the pH of the stock solution to between about 6.2 and 6.5.

3. The method of claim 2, wherein the buffer brings the pH of the stock solution to about 6.5.

4. The method of claim 1, wherein the stock solution further comprises an anesthetic.

5. The method of claim 4, wherein the anesthetic is bupivicaine.

6. The method of claim 1, wherein the concentration of chondroitin sulphate in the injectable is about 0.125% to 0.25%.

7. The method of claim 1, wherein the concentration of glucosamine HCl in the injectable is about 1.25% to 5%.

8. The method of claim 1, wherein the concentration of dextrose in the injectable is about 25%.

* * * * *